United States Patent [19]
Askin et al.

[11] Patent Number: 6,140,508
[45] Date of Patent: Oct. 31, 2000

[54] PROCESS FOR MAKING 1,5-DISUBSTITUTED IMIDAZOLES

[75] Inventors: David Askin, Warren; Jennifer A. Cowen, Somerville; Peter E. Maligres, Scotch Plains; J. Christopher McWilliams, Basking Ridge; Marjorie S. Waters, Cranbury, all of N.J.

[73] Assignee: Merck & Co., inc., Rahway, N.J.

[21] Appl. No.: 09/338,064

[22] Filed: Jun. 23, 1999

Related U.S. Application Data

[60] Provisional application No. 60/091,369, Jul. 1, 1998.

[51] Int. Cl.⁷ .................. C07D 403/02; C07D 233/56; C07D 233/60; C07D 233/61; C07D 233/54
[52] U.S. Cl. ...................... 548/336.1; 548/325.1; 548/335.1; 548/340.1; 548/341.1; 548/341.5; 548/342.1; 548/343.1
[58] Field of Search .............. 548/335.1, 336.1, 548/342.1

[56] References Cited

U.S. PATENT DOCUMENTS

| 5,710,171 | 1/1998 | Dinsmore et al. | 514/396 |
| 5,780,492 | 7/1998 | Dinsmore et al. | 514/397 |
| 5,869,682 | 2/1999 | DeSolms | 548/335.5 |

*Primary Examiner*—Floyd D. Higel
*Attorney, Agent, or Firm*—Dianne Pecoraro; Mark R. Daniel

[57] ABSTRACT

The present invention is directed to a process for synthesizing 1,5-disubstituted imidazoles, which are useful in the preparation of farnesyl-protein transferase inhibitors.

31 Claims, No Drawings

PROCESS FOR MAKING 1,5-DISUBSTITUTED IMIDAZOLES

DOMESTIC PRIORITY CLAIM

This application claims priority from the U.S. Provisional application No. 60/091,369, filed on Jul. 1, 1998.

BACKGROUND OF THE INVENTION

The Ras proteins are a family of guanine nucleotide binding GTPases that play a pivotal role in mediating cell growth, differentiation and development. (Barbacid, *Annual Review of Biochemistry*, Vol. 56, p. 779 (1987)). In mammalian cells, there are three ras genes that encode four Ras proteins, H, N, KA and KB-Ras. (E. C. Lerner et al., *Anti-Cancer Drug Design*, Vol. 12, pp. 229–238 (1997)). Mutations in Ha-ras, Ki-ras and N-ras, and the overexpression of Ras has been observed in approximately 30% of all human cancer tissues. (Lerner et al., S. L. Graham, *Exp. Opin. Ther. Patents*, Vol. 5, no. 12, pp. 1269–1285 (1995); T. Hiwasa, *Oncology Reports*, Vol. 3, pp. 7–14 (1996); S. L. Graham and T. M. Williams, *Exp. Opin. Ther. Patents*, Vol. 6, no. 12, pp. 1295–1304 (1996)). Although several steps are involved in modifying Ras proteins, farnesylation is the only step which is required and sufficient for Ras transforming activity. (E. C. Lerner et al.) Therefore, farnesyl-transferase (FTase) serves as an attractive target for the development of a potential new class of anti-cancer agents. (E. C. Lerner et al.) It has been noted that routes to inhibitors of Ras farnesylation are apparent from an examination of the substrate specificities of the enzyme. One can design analogs either of the lipid, or of the peptide sequence to which the lipid is transferred. Such compounds must be stable, and readily cross the cell membrane to gain access to the cytosolic transferase. (J. E. Buss and J. C. Marsters, Jr., *Chemistry and Biology*, Vol. 2, pp. 787–791 (1995)).

Compounds that incorporate 1,5 disubstituted imidazole moieties have been observed to be farnesyltransferase inhibitors. (WO 96/30343 published on Oct. 30, 1996). It is therefore desirable to discover a process for making 1,5 disubstituted imidazoles that is efficient, inexpensive, safe and operationally facile. Prior methods for synthesizing 1,5 disubstituted imidazoles involved using starting materials such as 5-hydroxymethylimidazole hydrochloride, which is expensive and not readily available in bulk. Such processes also utilized high molecular weight triphenylmethyl (trityl) protecting groups but these limit the efficiency of the process. The synthesis of 1,5 disubstituted imidazoles from primary amines, dihydroxyacetone and potassium thiocyanate via thioimidazoles has been reported in the classical synthetic chemical literature. (Marckwald, *Chem Ber.* 1892, 25, 2354) A more recent published example of this is by J. M. Duncia et al., *J. Med. Chem.* 1990, 33, 1312–1330. Literature protocols for the dethionation of 2-mercaptoimidazoles involved treatment with nitric acid. Such a procedure was found to result in the sudden and violent release of nitrogen oxide gases and gave variable results. The amine derivative could also be prepared using an azide displacement and reduction. However, the use of azides for such syntheses presents safety issues as well.

It is therefore an object of this invention to provide a process for the synthesis of 1,5 disubstituted imidazoles that employs commodity chemicals which are readily available and inexpensive.

It is a further object of this invention to provide a process for the synthesis of 1,5 disubstituted imidazoles that is more efficient by eliminating the use of high molecular weight trityl protecting groups.

It is a further object of this invention to provide a process for the synthesis of 1,5 disubstituted imidazoles that is safer by eliminating the use of azides and nitric acid.

SUMMARY OF THE INVENTION

The present invention is directed to the improved synthesis of compounds, as illustrated by formula I, which are useful in the preparation of farnesyl-protein transferase inhibitors.

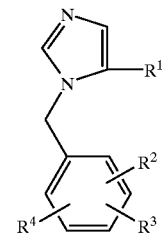

I

The instant invention is directed to a novel synthesis for 1,5 disubstituted imidazoles which is more efficient, economical and safer, than syntheses previously disclosed.

DETAILED DESCRIPTION OF THE INVENTION

The present invention is directed to the novel synthesis of compounds as illustrated by formula I:

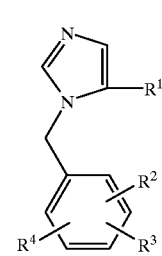

I wherein $R^1$ is selected from H, unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl; and $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, SO, $SO_2$, HC(O) ($C_0$–$C_6$ alkyl)—, ($C_1$–$C_6$ alkyl)C(O)($C_0$–$C_6$ alkyl)—, —N($R^{10}$)$_2$, —NH$R^{10}$, —NHC(O)$R^{10}$, —N($R^{10}$)C(O) $R^{10}$, —NHSO$_2$$R^{10}$, and —N($R^{10}$)SO$_2$$R^{10}$;

$R^2$ and $R^3$ or $R^3$ and $R^4$, when located on adjacent carbon atoms, may be joined in a ring;

$R^{10}$ is independently selected from unsubstituted or substituted $C_1$–$C_6$ alkyl, unsubstituted or substituted aryl, and unsubstituted or substituted aralkyl;

or the pharmaceutically acceptable salts, thereof;

which comprises the steps of:

a) treating a benzyl derivative of formula A

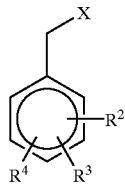

(where X is a suitable reactive leaving group and $R^2$, $R^3$ and $R^4$ are as defined above) with hexamethylenetetramine in an alcohol to produce a hexamethylenetetramine salt of formula A1

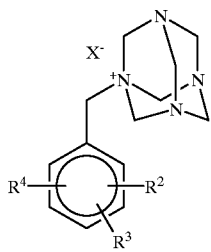

(where X, $R^2$, $R^3$ and $R^4$ are as defined above);

b) adding one or more acids to produce an amine salt of formula B

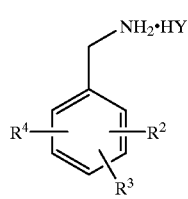

(where Y is selected from a halide, a sulfonate, a phosphate or a sulfate and $R^2$, $R^3$ and $R^4$ are as defined above);

c) reacting the amine salt of formula B with a mixture of a reagent selected from a hydroxyketone of formula C

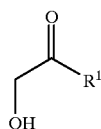

or a hydroxyketone dimer of formula D

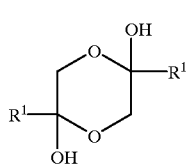

(wherein $R^1$ is as defined above) and a thiocyanate, in a suitable acidic solution to produce a mixture containing a mercapto-imidazole compound of formula E

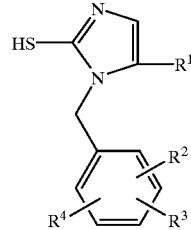

(where $R^1$, $R^2$, $R^3$ and $R^4$ are as defined above); and d) dethionating the mercapto-imidazole compound of formula E by treating with an oxidizing agent in an acidic solution to produce the compound of formula I.

In another embodiment, the process for synthesizing compounds of formula I

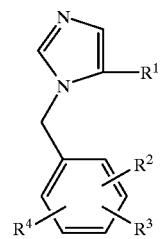

wherein $R^1$ is selected from H, unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl; and $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, SO, $SO_2$, HC(O)($C_0$–$C_6$ alkyl)—, ($C_1$–$C_6$ alkyl)C(O)($C_0$–$C_6$ alkyl)—, —N($R^{10}$)$_2$,—NH$R^{10}$, —NHC(O)$R^{10}$, —N($R^{10}$)C(O)$R^{10}$, —NHSO$_2$$R^{10}$, and —N($R^{10}$)SO$_2$$R^{10}$;

$R^2$ and $R^3$ or $R^3$ and $R^4$, when located on adjacent carbon atoms, may be joined in a ring;

$R^{10}$ is independently selected from unsubstituted or substituted $C_1$–$C_6$ alkyl, unsubstituted or substituted aryl, and unsubstituted or substituted aralkyl;

or the pharmaceutically acceptable salts, thereof;

further comprises the steps of:

a) treating a benzyl derivative of formula A

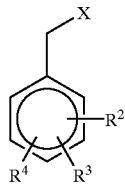

(where X is a suitable reactive leaving group and $R^2$, $R^3$ and $R^4$ are as defined above) with hexamethylenetetramine in an alcohol to produce a hexamethylenetetramine salt of formula A1

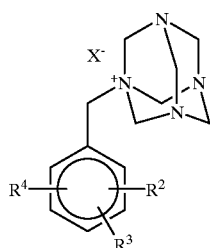

(where X, $R^2$, $R^3$ and $R^4$ are as defined above);

b) adding one or more acids to produce an amine salt of formula B

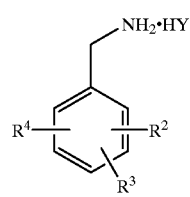

(where Y is selected from a halide or a phosphate and $R^2$, $R^3$ and $R^4$ are as defined above);

c) reacting the amine salt of formula B with a mixture of a reagent selected from a hydroxyketone of formula C

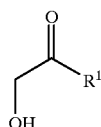

or a hydroxyketone dimer of formula D

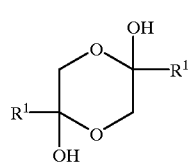

(wherein $R^1$ is as defined above) and a thiocyanate, in a suitable acidic solution to produce a mixture containing a mercapto-imidazole compound of formula E

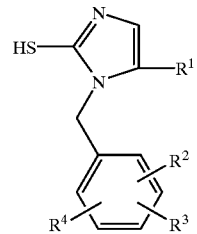

(where $R^1$, $R^2$, $R^3$ and $R^4$ are as defined above);

d) dethionating the mercapto-imidazole compound of formula E by adding an oxidizing agent, selected from a peroxide or a nitrite, in an acidic solution;

e) adding a base compound; and f) isolating the compound of formula I as a free base.

In another embodiment, the process for synthesizing compounds of formula I

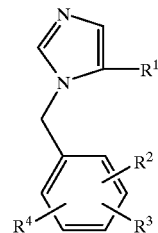

wherein $R^1$ is selected from H, unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl; and $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, SO, $SO_2$, HC(O)($C_0$–$C_6$ alkyl)—, ($C_1$–$C_6$ alkyl)C(O)($C_0$–$C_6$ alkyl)—, —N($R^{10}$)$_2$, —NH$R^{10}$, —NHC(O)$R^{10}$, —N($R^{10}$)C(O)$R^{10}$, —NHSO$_2$$R^{10}$, and —N($R^{10}$)SO$_2$$R^{10}$;

$R^2$ and $R^3$ or $R^3$ and $R^4$, when located on adjacent carbon atoms, may be joined in a ring;

$R^{10}$ is independently selected from unsubstituted or substituted $C_1$–$C_6$ alkyl, unsubstituted or substituted aryl, and unsubstituted or substituted aralkyl;

or the pharmaceutically acceptable salts, thereof;

further comprises the steps of:

a) treating a benzyl derivative of formula A

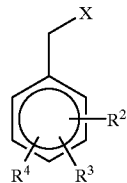

A (where X is a suitable reactive leaving group and $R^2$, $R^3$ and $R^4$ are as defined above) with hexamethylenetetramine in an alcohol to produce a hexamethylenetetramine salt of formula A1

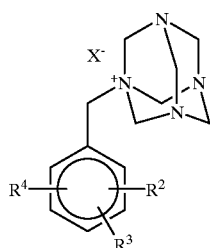

A1

(where X, $R^2$, $R^3$ and $R^4$ are as defined above);

b) treating the hexamethylenetetramine salt of formula A1 with phosphoric acid to produce a mixture containing an amine phosphate salt of formula B1

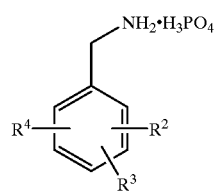

B1

(where $R^2$, $R^3$ and $R^4$ are as defined above);

c) reacting the mixture containing the amine phosphate salt of formula B1 with a mixture of a reagent selected from a hydroxyketone of formula C

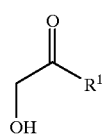

C or a hydroxyketone dimer of formula D

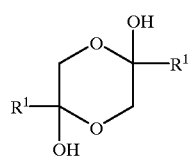

D (wherein $R^1$ is as defined above) and a thiocyanate, in a suitable acidic solution to produce a mixture containing a mercapto-imidazole compound of formula E

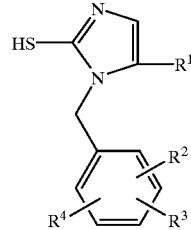

E (where $R^1$, $R^2$, $R^3$ and $R^4$ are as defined above);

d) dethionating the mercapto-imidazole compound of formula E by treating with an oxidizing agent, selected from a peroxide or a nitrite, in an acidic solution;

e) adding a base compound; and f) isolating the compound of formula I as a free base.

In another embodiment of the instant invention, the process or synthesizing compounds of formula I

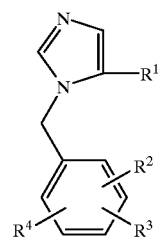

I wherein $R^1$ is selected from H, unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl; and $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, SO, $SO_2$, HC(O)($C_0$–$C_6$ alkyl)—, ($C_1$–$C_6$ alkyl)C(O)($C_0$–$C_6$ alkyl)—, —N($R^{10}$)$_2$, —NHR$^{10}$, —NHC(O)R$^{10}$, —N($R^{10}$)C(O)R$^{10}$, —NHSO$_2$R$^{10}$, and —N($R^{10}$)SO$_2$R$^{10}$;

$R^2$ and $R^3$ or $R^3$ and $R^4$, when located on adjacent carbon atoms, may be joined in a ring;

$R^{10}$ is independently selected from unsubstituted or substituted $C_1$–$C_6$ alkyl, unsubstituted or substituted aryl, and unsubstituted or substituted aralkyl;

or the pharmaceutically acceptable salts, thereof;

further comprises the steps of:

a) treating a benzyl derivative of formula A

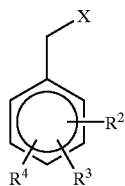

A (where X is a suitable reactive leaving group and $R^2$, $R^3$ and $R^4$ are as defined above) with hexamethylenetetramine in an alcohol to produce a hexamethylenetetramine salt of formula A1

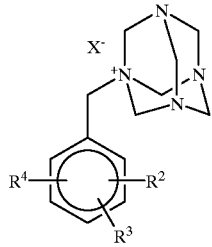

A1

(where X, $R^2$, $R^3$ and $R^4$ are as defined above);

b) treating the hexamethylenetetramine salt of formula A1 with HCl acid to produce a mixture containing an amine HCl salt
c) adding an anti-solvent;
d) recovering a precipitated amine HCl salt and adding a base compound to produce a free base;
e) converting the free base to a salt by adding an acid, producing a mixture containing an amine hydrochloride salt of formula B2

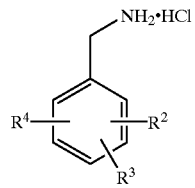

B2

(where $R^2$, $R^3$ and $R^4$ are as defined above);

f) reacting the mixture containing the amine salt of formula B2 with a mixture of a reagent selected from a hydroxyketone of formula C

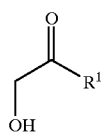

C or a hydroxyketone dimer of formula D

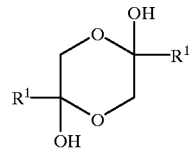

D (wherein $R^1$ is as defined above) and a thiocyanate, in a suitable acidic solution to produce a mixture containing a mercapto-imidazole compound of formula E

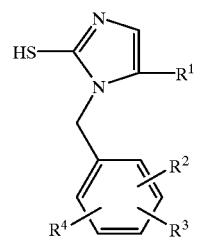

E (where $R^1$, $R^2$, $R^3$ and $R^4$ are as defined above);
  g) dethionating the mercapto-imidazole compound of formula E by treating with an oxidizing agent, selected from peroxides and nitrites, in an acidic solution;
  h) adding a base compound; and
  i) isolating the compound of formula I as a free base.

In a further embodiment of the instant invention, the process for synthesizing compounds of formula IA:

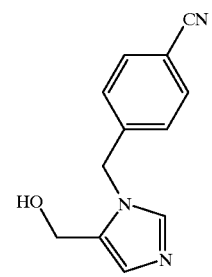

IA comprises the steps of:
  a) treating a cyanobenzyl bromide with hexamethylenetetramine in ethanol;
  b) adding one or more acids to produce a cyanobenzylamine salt;
  c) reacting the cyanobenzylamine salt with a mixture of dihydroxyacetone and potassium thiocyanate, in acidic solution to produce a mixture containing 1-(4-Cyanobenzyl)-2-Mercapto-5-Hydroxymethylimidazole;
  d) dethionating the 1-(4-Cyanobenzyl)-2-Mercapto-5-Hydroxymethylimidazole by treating with hydrogen peroxide in an acidic solution;
  e) adding ammonia;
  f) isolating 1-(4-Cyanobenzyl)-5-Hydroxymethylimidazole of formula IA as a free base.

In a second embodiment of the instant invention, the process for synthesizing compounds of formula IB

IB

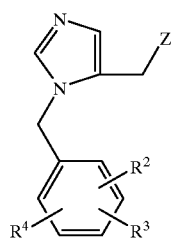

where $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, $SO$, $SO_2$, $HC(O)(C_0$–$C_6$ alkyl)—, $(C_1$–$C_6$ alkyl)$C(O)(C_0$–$C_6$ alkyl)—, —$N(R^{10})_2$, —$NHR^{10}$, —$NHC(O)R^{10}$, —$N(R^{10})C(O)R^{10}$, —$NHSO_2R^{10}$, and —$N(R^{10})SO_2R^{10}$;

$R^2$ and $R^3$ or $R^3$ and $R^4$, when located on adjacent carbon atoms, may be joined in a ring;

$R^{10}$ is independently selected from unsubstituted or substituted $C_1$–$C_6$ alkyl, unsubstituted or substituted aryl, and unsubstituted or substituted aralkyl;

Z is selected from a halide, a sulfonate, a phosphate or a sulfate;

comprises the step of:

combining a 1-substituted benzyl-5-hydroxymethylimidazole compound of formula IC

IC

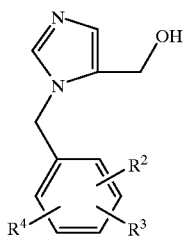

with an activating agent to produce a salt form of the compound of formula IB.

A further embodiment of the instant invention is the process hereinabove where Z of formula IB is a halide or mesylate and the activating agent is a halogenating agent or a sulfonating agent.

In a further embodiment of the instant invention, the process for synthesizing compounds of formula ID

ID

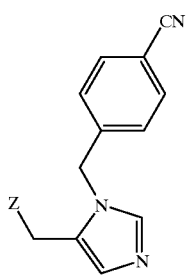

(where Z is a halide, a sulfate, a sulfonate, or a phosphonate) comprises the step of:

combining 1-(4-Cyanobenzyl)-5-Hydroxymethyl-imidazole of formula IA

IA

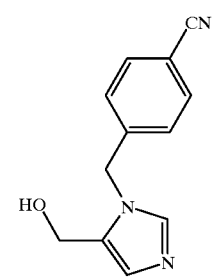

with an activating agent selected from a halogenating agent, a sulfating agent, a sulfonating agent, or a phosphonating agent to produce a compound of formula ID.

In a further embodiment of the instant invention, the process for synthesizing compounds of formula IE

IE

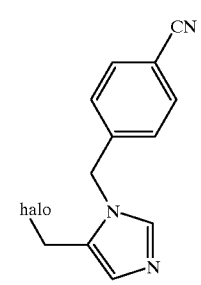

comprises the step of:

combining 1-(4-Cyanobenzyl)-5-Hydroxymethyl-imidazole of formula IA

IA

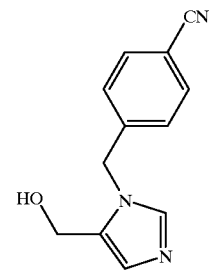

with a halogenating agent to produce a compound of formula IE.

In a further embodiment of the instant invention, the process further comprises:

combining 1-(4-Cyanobenzyl)-5-Hydroxymethyl-imidazole of formula IA

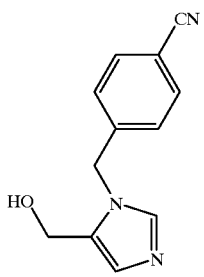

with Vilsmeier reagent to obtain 1-(4-Cyanobenzyl)-5-Chloromethylimidazole of formula IF:

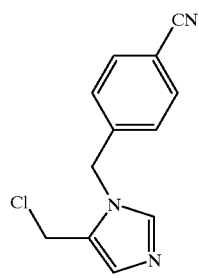

Compounds prepared using the process of the instant invention are useful as intermediates for making farnesyl protein transferase inhibitors, such as those described in WO 96/30343 which was published on Oct. 3, 1996 and U.S. Pat. No. 5,856,326, which issued on Jan. 5, 1999, and are herein incorporated by reference. Examples of compounds which can be made using the intermediates synthesized by the process of the instant invention include, but are not limited to, 5(S)-n-Butyl-1-(2,3-dimethylphenyl)-4-(4-imidazolylmethyl)-piperazin-2-one;

5(S)-n-Butyl-4-[1-(4-cyanobenzyl)imidazol-5-ylmethyl]-1-(2,3-dimethylphenyl)piperazin-2-one;

4-[1-(4-Cyanobenzyl)imidazol-5-ylmethyl]-1-(2,3-dimethylphenyl)-5(S)-(2-methoxyethyl)piperazin-2-one;

(S)-1-(3-Chlorophenyl)-4-[1-(4-cyanobenzyl)-5-imidazolylmethyl]-5-[2-(methanesulfonyl)ethyl]-2-piperazinone;

(S)-1-(3-Chlorophenyl)-4-[1-(4-cyanobenzyl)-5-imidazolylmethyl]-5-[2-(ethanesulfonyl)ethyl]-2-piperazinone;

(S)-1-(3-Chlorophenyl)-4-[1-(4-cyanobenzyl)-5-imidazolylmethyl]-5-[2-(ethanesulfonyl)methyl]-2-piperazinone;

(S)-1-(3-Chlorophenyl)-4-[1-(4-cyanobenzyl)-5-imidazolylmethyl]-5-[N-ethyl-2-acetamido]-2-piperazinone;

(±)-5-(2-Butynyl)-1-(3-chlorophenyl)-4-[1-(4-cyanobenzyl)-5-imidazolylmethyl]-2-piperazinone;

1-(3-Chlorophenyl)-4-[1-(4-cyanobenzyl)-5-imidazolylmethyl]-2-piperazinone;

5(S)-Butyl-4-[1-(4-cyanobenzyl-2-methyl)-5-imidazolylmethyl]-1-(2,3-dimethylphenyl)-piperazin-2-one;

4-[1-(2-(4-Cyanophenyl)-2-propyl)-5-imidazolylmethyl]-1-(3-chlorophenyl)-5(S)-(2-methylsulfonylethyl)piperazin-2-one;

5(S)-n-Butyl-4-[1-(4-cyanobenzyl)-5-imidazolylmethyl]-1-(2-methylphenyl)piperazin-2-one;

4-[1-(4-Cyanobenzyl)-5-imidazolylmethyl]-5(S)-(2-fluoroethyl)-1-(3-chlorophenyl)piperazin-2-one;

4-[5-(4-Cyanobenzyl)-1-imidazolylethyl]-1-(3-chlorophenyl)piperazin-2-one;

or the pharmaceutically acceptable salts, thereof.

As used herein, "alkyl" is intended to include both branched and straight-chain saturated aliphatic hydrocarbon groups having 1 to 6 carbon atoms, unless otherwise specified; "alkoxy" represents an alkyl group having 1 to 6 carbon atoms, unless otherwise indicated, attached through an oxygen bridge. "Halogen" or "halo" as used herein means fluoro, chloro, bromo and iodo.

As used herein, "halide" means chloride, bromide, iodide and fluoride. The term "sulfate" is intended to include, but is not limited to, a substituted or unsubstituted alkyl or aryl sulfate such as methylsulfate, ethylsulfate, propylsulfate, chloromethylsulfate, trichloromethylsulfate, trifluoromethylsulfate, trifluoroethylsulfate, phenylsulfate, tolylsulfate, nitrophenylsulfate, chlorophenylsulfate, bromophenylsulfate and the like. The term "sulfonate" is intended to include, but is not limited to, a substituted or unsubstituted alkyl or aryl sulfonate, such as methanesulfonate, ethanesulfonate, propanesulfonate, chloromethanesulfonate, trichloromethanesulfonate, trifluoromethanesulfonate, trifluoroethanesulfonate, benzenesulfonate, toluenesulfonate, nitrobenzenesulfonate, chlorobenzenesulfonate, bromobenzenesulfonate, and the like. The term "phosphate" is intended to include, but is not limited to, a substituted or unsubstituted alkyl or aryl phosphate, such as methylphosphate, ethylphosphate, propylphosphate, chloromethylphosphate, trichloromethylphosphate, trifluoromethylphosphate, trifluoroethylphosphate, phenylphosphate, tolylphosphate, nitrophenylphosphate, chlorophenylphosphate, bromophenylphosphate, and the like.

As used herein, "aryl", and the "aryl" part of aryloxy, is intended to mean any stable monocyclic or bicyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, "aralkyl" is intended to mean an aryl moiety, as defined above, attached through a $C_1$–$C_6$ alkyl linker, where alkyl is defined above. Examples of aralkyls inlcude, but are not limited to, benzyl, naphthylmethyl and phenylpropyl.

As used herein, "heteroaralkyl" is intended to mean a heteroalkyl moiety, as defined above, attached through a $C_1$–$C_6$ alkyl linker, where alkyl is defined above. Examples of heteroaralkyls include, but are not limited to, 2-pyridylmethyl, 2-imidazolylethyl, 2-quinolinylmethyl, 2-imidazolylmethyl, 1-(2-oxopiperidinyl)methyl, and the like As used herein, the terms "substituted $C_1$–$C_6$ alkyl" and "substituted $C_1$–$C_6$ alkoxy" is intended to include the branch or straight-chain alkyl group of the specified number of carbon atoms, wherein the carbon atoms may be substituted with F, Cl, Br, I, $CF_3$, $NH_2$, $N(C_1$–$C_6$ alkyl$)_2$, $N_3$, CN, $NO_2$, $C_1$–$C_{20}$ alkyl, oxo, —OH, —O($C_1$–$C_6$ alkyl), ($C_0$–$C_6$ alkyl)$S(O)_{0-2}$—, $C_3$–$C_{10}$ cycloalkyl, $C_2$–$C_6$ alkenyl, $C_2$–$C_6$ alkynyl, —C(O)NH, ($C_1$–$C_6$ alkyl)C(O)NH—, $H_2N$—C(NH)—, ($C_0$–$C_6$ alkyl)C(O)—, —O($C_0$–$C_6$ alkyl)$CF_3$, ($C_0$–$C_6$ alkyl)OC(O)—, ($C_0$–$C_6$ alkyl)O($C_0$–$C_6$ alkyl)—, ($C_0$–$C_6$ alkyl)C(O)2($C_0$–$C_6$ alkyl)—, ($C_0$–$C_6$ alkyl)OC(O)NH—, —$NHR^{10}$, —$NHC(O)R^{10}$, —$N(R^{10})C(O)R^{10}$, —$NHSO_2R^{10}$, —$N(R^{10})SO_2R^{10}$, aryl, heteroaryl, aralkyl, heteroaralkyl, halo-aryl, halo-heteroaryl, halo-aralkyl, halo-heteroaralkyl, cyano-aryl, cyano-aralkyl, cyano-heteroaryl and cyano-heteroaralkyl.

As used herein, the terms "substituted aryl", "substituted heteroaryl", "substituted aralkyl" and "substituted heteroaralkyl" are intended to include the cyclic group containing from 1 to 3 substitutents in addition to the point of attachment to the rest of the compound. Such substitutents are preferably selected from the group which includes but is not limited to F, Cl, Br, I, $CF_3$, $NH_2$, $N(C_1$–$C_6$ alkyl$)_2$, $NO_2$, CN, $N_3$, $C_1$–$C_{20}$ alkyl, oxo, —OH, —O($C_1$–$C_6$ alkyl), ($C_0$–$C_6$ alkyl)$S(O)_{0-2}$, $C_3$–$C_{10}$ cycloalkyl, $C_2$–$C_6$ alkenyl, $C_2$–$C_6$ alkynyl, —C(O)NH, ($C_1$–$C_6$ alkyl)C(O)NH—, $H_2N$—C(NH)—, ($C_0$–$C_6$ alkyl)C(O)—, —O($C_0$–$C_6$ alkyl)$CF_3$, ($C_0$–$C_6$ alkyl)OC(O)—, ($C_0$–$C_6$ alkyl)O($C_0$–$C_6$ alkyl)—, ($C_0$–$C_6$ alkyl)C(O)$_2$($C_0$–$C_6$ alkyl)—, ($C_0$–$C_6$ alkyl)OC(O)NH—, —$NHR^{10}$, —$NHC(O)R^{10}$, —$N(R^{10})C(O)R^{10}$, —$NHSO_2R^{10}$, —$N(R^{10})SO_2R^{10}$, aryl, heteroaryl, aralkyl, heteroaralkyl, halo-aryl, halo-heteroaryl, halo-aralkyl, halo-heteroaralkyl, cyano-aryl, cyano-aralkyl, cyano-heteroaryl and cyano-heteroaralkyl.

When $R^2$ and $R^3$ or $R^3$ and $R^4$ are combined to form a ring, cyclic alkyl moieties are formed. Examples of such cyclic moieties include, but are not limited to,

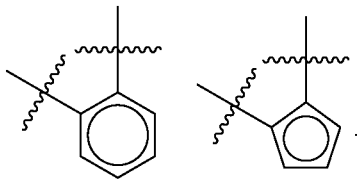

Lines drawn into the ring systems from substituents (such as from $R^2$, $R^3$, $R^4$, etc.) indicate that the indicated bond may be attached to any of the substitutable ring carbon atoms.

Preferably, $R^1$ of formula I is selected from H, unsubstituted or substituted aryl, unsubstituted or substituted heteroaralkyl and unsubstituted or substituted $C_1$–$C_6$ alkyl. More preferably, $R^1$ is selected from unsubstituted or substituted $C_1$–$C_6$ alkyl. Most preferably, $R^1$ is 3-chloromethyl.

Preferably, $R^2$, $R^3$ and $R^4$ of the benzyl derivative of formula A are independently selected from H, CN, halo, nitro, OH, unsubstituted or substituted $C_1$–$C_6$ alkyl, unsubstituted or substituted $C_1$–$C_6$ alkoxy, $NO_2$, trihalo-$C_1$–$C_6$ alkyl, trihalo-$C_1$–$C_6$ alkoxy, SO, $SO_2$, or ($C_1$–$C_6$ alkyl)C(O)($C_0$–$C_6$ alkyl)—. More preferably, $R^2$, $R^3$ and $R^4$ are independently selected from H, halo, CN, nitro, unsubstituted or substituted $C_1$–$C_6$ alkyl, or OH. Still more preferably, $R^2$, $R^3$ and $R^4$ are independently selected from H, halo, CN or nitro. Most preferably, $R^2$ and $R^4$ are hydrogen and $R^3$ is p-CN.

Preferably, X of formula A is selected from halides, sulfonates, phosphates, sulfates, sulfite, borate, boronate, trialkyl silyl, acetate or other carboxylic esters, 2-pyridyl or other nitrogen heterocycle derivatives. More preferably, X of formula A is selected from halides, sulfonates, phosphates or sulfates. Still more preferably, X is a halide. Most preferably, X is bromide.

Preferably, Z of formula IB is selected from a halide or a sulfonate. Most preferably, Z is Cl, Br or mesylate.

Abbreviations used throughout the specification include:

| | |
|---|---|
| ACN | acetonitrile |
| $Ac_2O$ | acetic anhydride; |
| Boc | t-Butoxycarbonyl; |
| CBz | Carbobenzyloxy; |
| DBU | 1,8-diazabicyclo[54.0]undec-7-ene; |
| DEAD | diethylazodicarboxylate |
| DEM | diethoxymethane |
| DIAD | diisopropylazodicarboxylate |
| DIEA | diisopropylethylamine |
| DPAD | dipiperidineazodicarbonyl |
| DMA | N,N-dimethylacetamide |
| DMAP | 4-Dimethylaminopyridine; |
| DME | 1,2-Dimethoxyethane; |
| DMF | Dimethylformamide; |
| DMPU | 1,3-Dimethyl-3,4,5,6-tetrahydro-2-(1H)-pyrimidinone |
| DMSO | Dimethyl sulfoxide |
| EDC | 1-(3-dimethylaminopropyl)-3-ethyl-carbodiimidehydrochloride; |
| $Et_3N$ | Triethylamine; |
| EtOAc | Ethyl acetate; |
| FAB | Fast atom bombardment; |
| HMTA | Hexamethylenetetramine |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MEK | Methyl ethyl ketone |
| MIBK | Methyl isobutyl ketone |
| MsCl | Methanesulfonyl chloride; |
| MsOH | methanesulfonic acid |
| MTBE | methyl-t-butyl-ether |
| NaHMDS | Sodium bis(trimethylsilyl)amide; |
| NMP | N-Methyl pyrrolidinone |
| ODCB | Ortho Dichlorobenzene, or 1,2-dichlorobenzene |
| Py | Pyridine; |
| TFA | Trifluoroacetic acid; |
| THF | Tetrahydrofuran; |
| TsOH | P-Toluenesulfonic acid |

The compounds synthesized by the invention are prepared by employing reactions as shown in Schemes 1–4.

These reactions may be employed in a linear sequence to provide the compounds of the formula I or they may be used to synthesize fragments which are subsequently joined by the reductive alkylation or acylation reactions described in the Schemes.

SCHEME 1
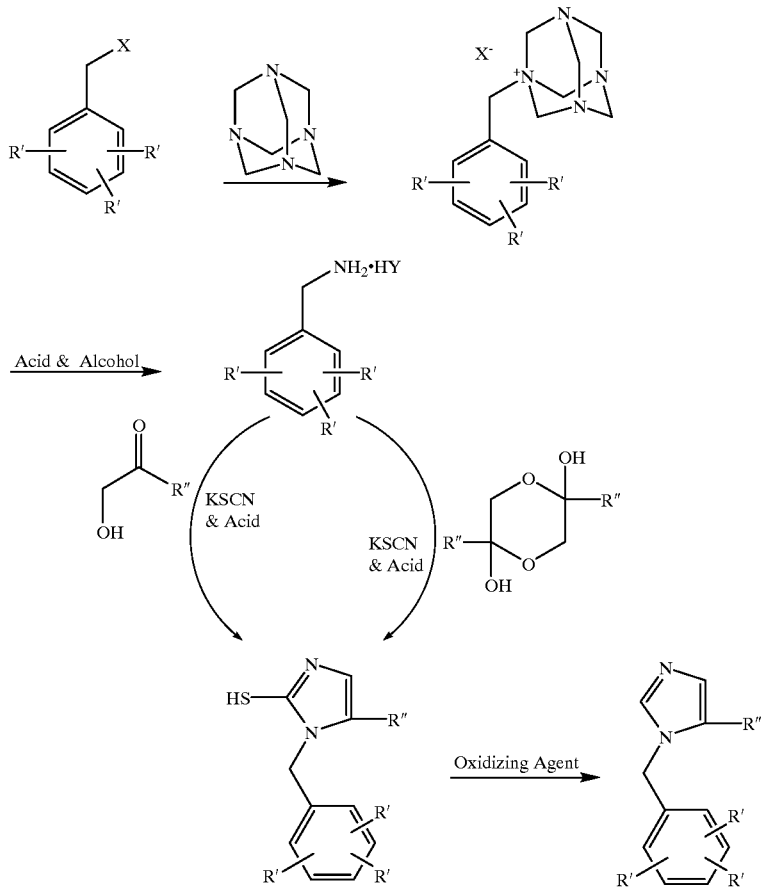
SCHEME 2
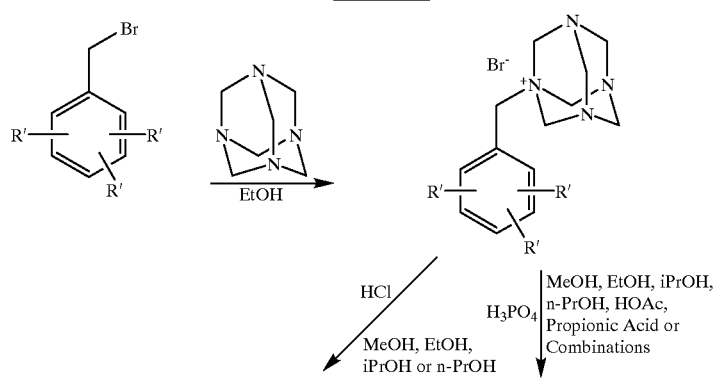

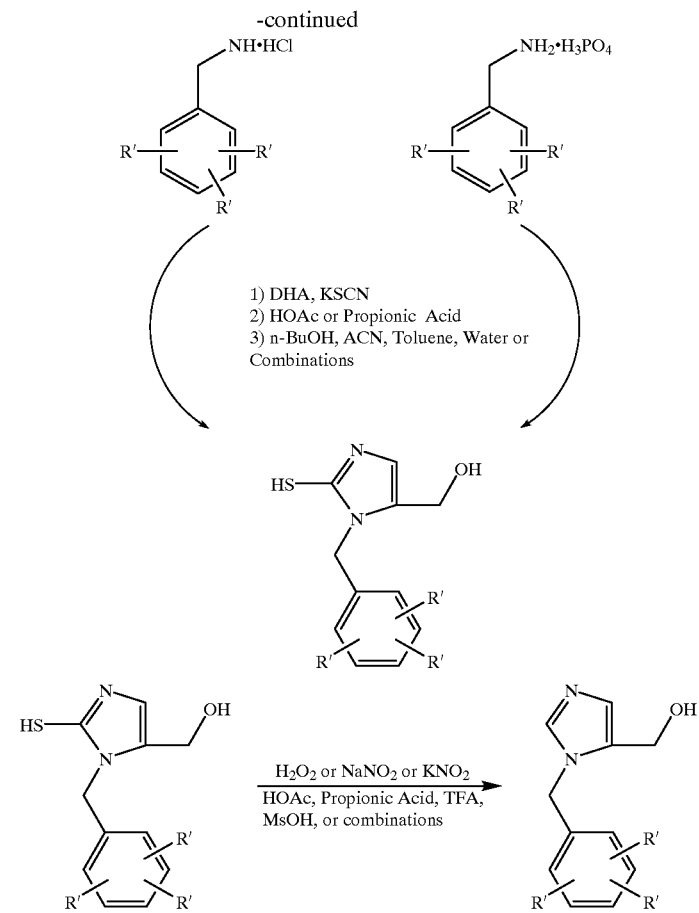
SCHEME 3
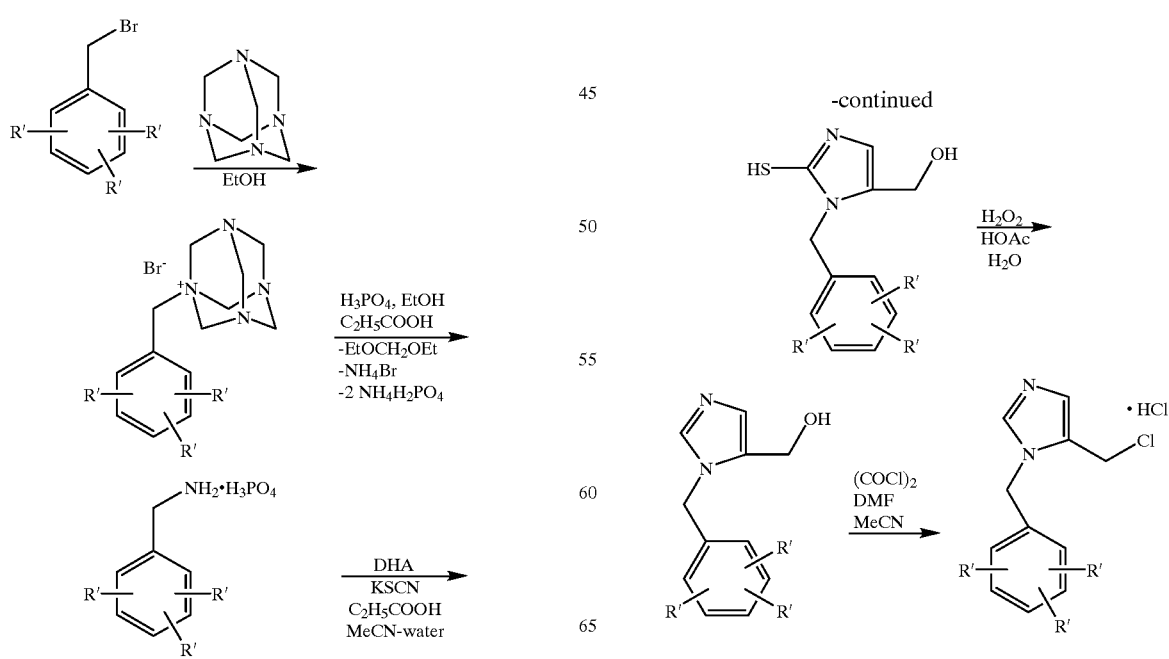

SCHEME 4

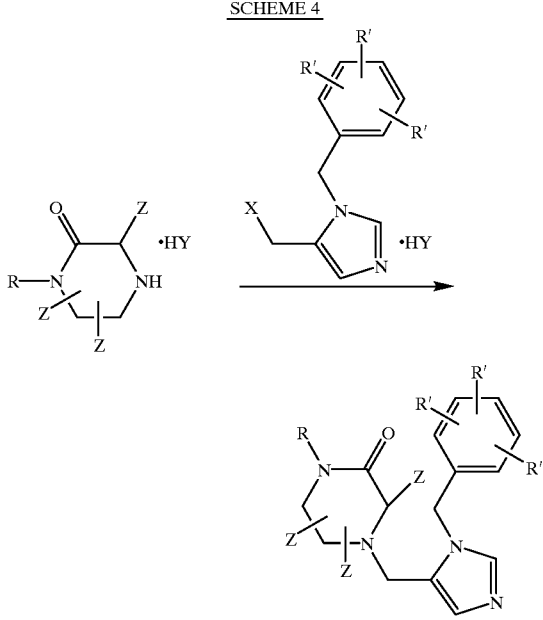

In the above Schemes, it is understood that

R' independently represents $R^2$, $R^3$ and $R^4$ or a protected precursor thereof;

R" independently represents $R^1$ or a protected precursor thereof;

R represents unsubstituted or substituted aryl, unsubstituted or substituted heteroaryl, unsubstituted or substituted aralkyl, and unsubstituted or substituted heteroaralkyl;

X and Y are independently selected from a halide, a sulfonate, a phosphate or a sulfate;

Z independently represents
  a) H,
  b) unsubstituted or substituted $C_1$–$C_6$ alkyl,
  c) unsubstituted or substituted aryl,
  d) unsubstituted or substituted heteroaryl,
  e) unsubstituted or substituted aralkyl,
  f) unsubstituted or substituted heteroaralkyl,
  g) unsubstituted or substituted $C_1$–$C_6$ alkoxy,
  h) $C_1$–$C_6$ alkynyl,
  i) $OCF_3$, and
  j) $CF_3$;

DHA represents dihydroxacetone in equilibrium with its dimer, as shown by the following scheme:

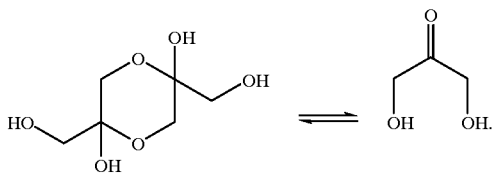

Types of solvents that may be used for the reactions of the present invention may include, but are not limited to, water, alcohols, unchlorinated or chlorinated hydrocarbons, nitrites, ketones, ethers, polar aprotic solvents or mixtures thereof. Types of alcohols that can be used include, but are not limited to, methanol, ethanol, n-propanol, i-propanol, butanol or an alkoxyethanol. Types of unchlorinated hydrocarbons include, but are not limited to, toluene or xylene. Types of chlorinated hydrocarbons include, but are not limited to, dichloromethane, chloroform, chlorobenzene or ODCB. Types of nitrites include, but are limited to, acetonitrile, propionitrile, benzonitrile or tolunitrile. Types of ketones include, but are not limited to, acetone, MEK, MIBK and cyclohexanone. Types of ethers include, but are not limited to, diethyl ether, MTBE, THF, DME and DEM. Types of polar aprotic solvents include, but are not limited to, formamide, DMF, DMA, NMP, DMPU, DMSO, and sulfolane.

The present invention relates to an improved synthesis for 1,5 disubstituted imidazoles. The first step in this process requires treating a benzyl derivative of formula A

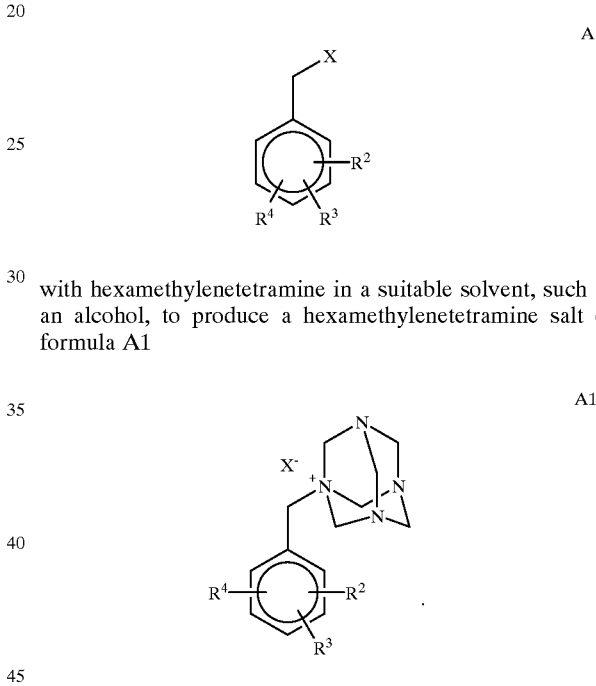

with hexamethylenetetramine in a suitable solvent, such as an alcohol, to produce a hexamethylenetetramine salt of formula A1

In Formulae A and A1, $R^2$, $R^3$ and $R^4$ are as defined above. Preferably, the benzyl moiety is substituted with cyano. Types of suitable reactive leaving groups, designated as X, that may be located on the benzyl moiety include, but are not limited to, a halide, a sulfonate, a phosphate, a sulfate, sulfite, borate, boronate, trialkyl silyl, acetate or other carboxylic esters, 2-pyridyl or other nitrogen heterocycle derivatives. Preferably, X is a halide, a sulfonate, a phosphate or a sulfate. More preferably, an unsubstituted or substituted benzyl halide is used. Preferably, an alcohol, as described previoulsy is used. More preferably, the alcohol is methanol, ethanol, n-propanol, i-propanol, butanol or an alkoxyethanol. Most preferably, a para-cyanobenzyl bromide is treated with hexamethylenetetramine in ethanol.

The hexamethylenetetramine salt of formula A1 is then mixed with one or more acids to produce an amine salt of formula B

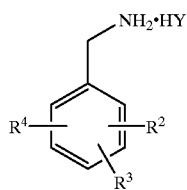

(where Y is selected from a halide, a sulfonate, a phosphate or a sulfate and $R^2$, $R^3$ and $R^4$ are as defined above). Types of acids that can be used include, but are not limited to, anhydrous or aqueous HF, HCl, HBr, HI, sulfuric, monophosphate salt, di-phosphate salt, mixed phosphate salt, phosphoric, propionic, MsOH, TsOH, carboxylic acids or ammonium halides. A mixed phosphate salt can be illustrated as $M_1M_2HPO_4$, where $M_1$ and $M_2$ are independently selected from H, Na, K, $NH_4OH$, sodium potassium, and the like. More preferably, the acids are selected from aqueous or anhydrous propionic, phosphoric and HCl. For this embodiment, most preferably, a combination of propionic and phosphoric acid are used and an amine phosphate salt of formula B1

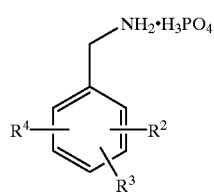

(where $R^2$, $R^3$ and $R^4$ are as defined above) is obtained. Preferably, the phosphoric acid is added gradually, over about 5 to about 10 minutes, while maintaining the temperature below about 65° C. The salt-containing mixture is then heated to a temperature between about 65° C. to about 70° C. over about 15 to about 45 minutes, followed by cooling to a temperature of about 15° C. to about 35° C.

In another embodiment of the present invention, hydrochloric acid is used to produce an amine salt. An anti-solvent is then added to produce a precipitate-containing solution. Types of anti-solvents include, but are not limited to, ethyl acetate, THF, MTBE, toluene, acetonitrile, DMF, alcohols, or carboxylic acids. Preferably, ethyl acetate is used. The precipitate-containing solution is then filtered and the precipitated salt is recovered, converted to a free base and extracted into a solvent, as described previously. Types of base compounds that may be used to convert the salt to a free base include, but are not limited to, $Et_3N$, DIPEA, n-$Bu_3N$, Imidazole, N-Me-imidazole, Pyridine, 2,6-Lutidine, 2,4,6-Collidine, 2,6-t$Bu_2$-pyridine, 2,6-t-$Bu_2$-4-Me-pyridine, DMAP, DBU, DBN, DABCO, N-Me-morpholine, N-Et-morpholine, 1,2,2,6,6-$Me_5$-piperidine, $Me_4$-guanidine, Proton Sponge, N,N-$Me_2$-aniline, N,N-$Et_2$-aniline, Quinoline, i-$Pr_2$NH, $Cyclohex_2$NH, Cyclohex, iPrNH, Pyrrolidine, Piperidine, 2,2,6,6-$Me_4$-piperidine, $TMS_2$NH (HMDS), $LiNH_2$, $NaNH_2$, $KNH_2$, LHMDS, NaHMDS, KHMDS, $BnNMe_3OMe$, NaOEt, TlOEt, LiOt-Bu, NaOt-Bu, KOt-Bu, LiOt-Am, NaOt-Am, KOt-Am, KH, KOTMS, NaOH, KOH, n-$Bu_4$NOH, Triton-B, $Ca(OH)_2$, CaO, BaO, $Na_2SO_3$, $Li_2CO_3$, $Na_2CO_3$, $K_2CO_3$, $Cs_2CO_3$, $NH_4OH$, $(NH_4)_2CO_3$, Guanidine carbonate, $CaCO_3$, $NaHCO_3$, $KHCO_3$, and $K_3PO_4$. Preferably, NaOH, KOH or $NH_4OH$ is used. The free base is then converted to a salt by adding an acid, as described previously. For this embodiment, it is preferred that aqueous HCl is used and an amine hydrochloride salt of formula B2

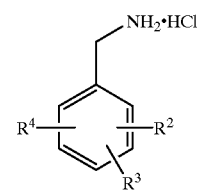

(where $R^2$, $R^3$ and $R^4$ are as defined above) is obtained.

The amine salt of formula B1 or B2, as described above, is then reacted with a mixture of a reagent, comprising hydroxyketone, its dimeric equivalent (as represented below by formulae C and D) or DHA, and a thiocyanate in a suitable acidic solution to produce a mercaptoimidazole of formula E

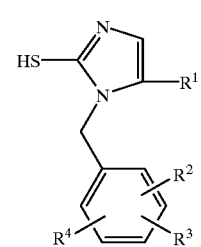

(where $R^1$, $R^2$, $R^3$ and $R^4$ are as defined above). Preferably, the amine phosphate salt of formula BI is used. Formula C represents a hydroxyketone

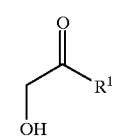

and formula D represents a hydroxyketone dimer

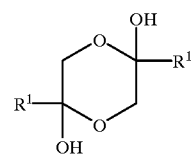

where $R^1$ is as defined hereinabove, or a protected precursor thereof. Preferably, dihydroxyacetone, its dimeric equivalent or DHA, which represents the dihydroxyacetone and its dimer in equilibrium, as shown below, is used.

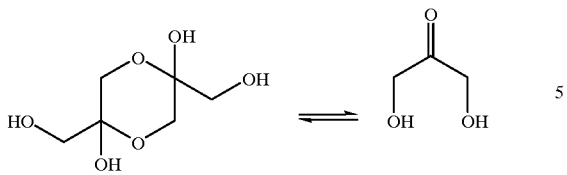

Most preferably, DHA is used.

Types of thiocyanates that may be used include, but are not limited to, $C_1-C_6$ alkyl-SCN, aryl-SCN, heteroaryl-SCN, LiSCN, NaSCN, KSCN, CsSCN, MgSCN, CaSCN, HSCN, $NH_4SCN$ or TMS-SCN. Types of suitable acidic solutions that may be used include, but are not limited to, one of the acids described previously in a solution containing acetonitrile, water, toluene or a mixture of these, with or without n-butanol. Preferably, the salt is mixed with dihydroxyacetone and KSCN, in the presence of propionic or acetic acid. Preferably, the solvents used are selected from acetonitrile or a mixture of acetonitrile and toluene, which may or may not contain water. Preferably, the mixture is then heated to a temperature of about 45° C. to about 75° C. and seed is added. Then the mixture is aged, heated, aged, cooled to a temperature of about 5° C. to about 10° C. and aged again. Each time, the mixture was aged for about 1 to about 3 hours.

The mercapto-imidazole compound of formula E is then dethionated by treating the compound with an oxidizing agent in an acidic solution to produce a dethionated imidazole. Types of oxidizing agents that may be used include, but are not limited to, peroxides and nitrites. Types of peroxides include, but are not limited to, hydrogen peroxide, peracetic acid, MCPBA and t-BuOH. Types of nitrites include, but are not limited to, $NaNO_2$, $KNO_2$, and $C_1-C_6$ alkyl-$NO_2$. Preferably, the acidic solution used is aqueous methanesulfonic acid, acetic acid, propionic acid, trifluoroacetic acid or a mixture thereof. Most preferably, hydrogen peroxide and a mixture of acetic acid, trifluoroacetic acid and methanesulfonic acid is used. Preferably, the oxidizing agent is added over about 2 to about 3 hours, while maintaining the temperature between about 35° C. to about 45° C. during addition of the agent. Preferably, the dethionated imidazole is then heated, aged and cooled.

In a further embodiment of the instant invention, a base compound, as described previously, is added next. Preferably, the base compound is $NH_4OH$, $Na_2SO_3$, KOH, NaOH. Any residual oxidizing agent is neutralized and a compound of formula I is isolated. Preferably, a 1-substituted benzyl-5-hydroxymethylimidazole compound of formula IC

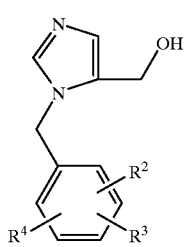

IC is obtained.

In a further embodiment, a compound of formula IC is combined with an activating agent to obtain a compound of formula IB

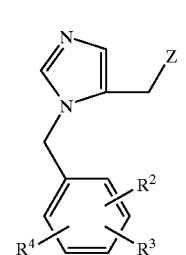

IB

Types of 1-substituted benzyl-5-hydroxymethyl imidazole of formula IC that can be used include, but are not limited to, benzyl-hydroxymethyl imidazoles where the benzyl moiety contains from 1 to 3 substituents in addition to the point of attachment to the rest of the compound. Examples of such substituents may include, but are not limited to, cyano, halo, nitro, unsubstituted or substituted $C_1-C_6$ alkoxy, unsubstituted or substituted aryl, unsubstituted or substituted heteroaryl and unsubstituted or substituted $C_1-C_6$ alkyl. Z comprises a halide, a sulfonate, a phosphate or a sulfate.

Types of activating agents that may be used include, but are not limited to, halogenating reagents, sulfonating reagents, sulfating reagents, phosphonating reagents or fluorinating reagents. Types of halogenating agents that may be used include, but are not limited to, inorganic acid halides, organic acid halides, cyanuric chloride, Vilsmeier reagent, Phosgene imminium chloride, Gold's reagent, chlorinated heterocycles and combinations of halogenating agents such as halogens, $CCl_4$, $C_2Cl_6$, or other alkyl halides with reducing agents such as triaryl or trialkyl phosphines or phosphites or a hydrogen halide in the presence of a dehydrating agent. Examples of sulfonating reagents include, but are not limited to, methanesulfonyl chloride (mesyl chloride), methanesulfonic anhydride, ethanesulfonyl chloride, benzenesulfonyl chloride, p-toluenesulfonyl chloride, dansyl chloride, triisopropylbenzenesulfonyl chloride, mesitylenesulfonyl chloride, naphthalenesulfonyl chloride, and quinolinesulfonyl chloride. Examples of sulfating reagents include, but are not limited to, sulfuric acid, chlorosulfonic acid, pyridine-1-sulfate, trimethylsilyl chlorosulfonate, sulfur trioxide, and the Burgess reagent. Examples of phosphonating reagents include, but are not limited to, trialkylphosphates (such as trimethylphosphate, triethylphosphate, triphenylphosphate and the like), dialkyl chlorophosphates (such as diphenyl chlorophosphate, dimethyl chlorophosphate, diethyl chlorophosphate, diisopropylchlorophosphate, bis(2,2,2-trichloroethyl) phosphorochloridate, 1,2-phenylene phosphorochloridate, ethylene chlorophosphate and the like), and phosphoric acid. An example of a fluorinating reagent is DAST (Diethylaminosulfur trifluoride).

Preferably, a halogenating or sulfonating agent is used. Preferably, the halogenating agent is selected from the group consisting of $SOCl_2$, $POCl_3$, oxalyl chloride, mesyl chloride, cyanuric chloride or Vilsmeier reagent. More preferably, the halogenating agent is selected from $SOCl_2$, $POCl_3$, $SOBr_2$, $POBr_3$, oxalyl chloride, or Vilsmeier reagent. Preferably, the sulfonating agent is selected from methanesulfonyl chloride (mesyl chloride), methanesulfonic anhydride, mesitylenesulfonyl chloride, and p-toluenesulfonyl chloride. More preferably, methanesulfonyl chloride (mesyl chloride) is used.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of p-Cyanobenzylamine.$H_3PO_4$ salt

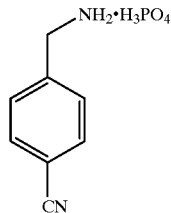

A slurry of HMTA in 2.5 L EtOH was added gradually over about 30 min to about 60 min to a stirred slurry of cyanobenzyl-bromide in 3.5 L EtOH and maintained at about 48–53° C. with heating & cooling in a 22 L neck flask (small exotherm). Then the transfer of HMTA to the reaction mixture was completed with the use of 1.0 L EtOH. The reaction mixture was heated to about 68–73° C. and aged at about 68–73° C. for about 90 min. The reaction mixture was a slurry containing a granular precipitate which quickly settled when stirring stopped.

The mixture was cooled to a temperature of about 50° C. to about 55° C. Propionic acid was added to the mixture and the mixture was heated and maintained at a temperature of about 50° C. to about 55° C. Phosphoric acid was gradually added over about 5 min to about 10 min, maintaining the reaction mixture below about 65° C. to form a precipitate-containing mixture. Then the mixture was gradually warmed to about 65° C. to about 70° C. over about 30 min and aged at about 65° C. to about 70° C. for about 30 min. The mixture was then gradually cooled to about 20–25° C. over about 1 hour and aged at about 20–25° C. for about 1 hour.

The reaction slurry was then filtered. The filter cake was washed four times with EtOH, using the following sequence, 2.5 L each time. The filter cake was then washed with water five times, using 300 mL each time. Finally, the filter cake was washed twice with MeCN (1.0 L each time) and the above identified compound was obtained.

EXAMPLE 2

Preparation of 4-Cyanobenzylamine Hydrochloride via Hexamethylenetetrammonium salt

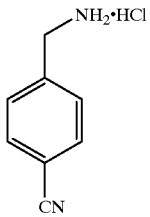

A 72 liter vessel was charged with 190 proof ethanol (14.4 L) followed by the addition of 4-cyanobenzylbromide (2.98 kg) and HMTA (2.18 kg) at ambient temperature. The mixture was heated to about 72–75° C. over about 60 min. On warming, the solution thickens and additional ethanol (1.0 liter) was added to facilitate stirring. The batch was aged at about 72–75° C. for about 30 min.

The mixture was allowed to cool to about 20° C. over about 60 min, and HCl gas (2.20 kg) was sparged into the slurry over about 4 hours during which time the temperature rose to about 65° C. The mixture was heated to about 70–72° C. and aged for about 1 hour. The slurry was cooled to about 30° C. and ethyl acetate (22.3 L) added over about 30 min. The slurry was cooled to about –5° C. over about 40 min and aged at about –3 to about –5° C. for about 30 min. The mixture was filtered and the crystalline solid was washed with chilled ethyl acetate (3×3 L). The solid was dried under a $N_2$ stream for about 1 hour before charging to a 50 liter vessel containing water (5.5 L). The pH was adjusted to about 10–10.5 with 50% NaOH (4.0 kg) maintaining the internal temperature below about 30° C. At about 25° C., methylene chloride (2.8 L) was added and stirring continued for about 15 min. The layers were allowed to settle and the lower organic layer was removed. The aqueous layer was extracted with methylene chloride (2×2.2 L). The combined organic layers were dried over potassium carbonate (650 g). The carbonate was removed via filtration and the filtrate concentrated in vacuo at about 25° C. to give a free base as a yellow oil.

The oil was transferred to a 50 liter vessel with the aid of ethanol (1.8 L). Ethyl acetate (4.1 L) was added at about 25° C. The solution was cooled to about 15° C. and HCl gas (600 g) was sparged in over about 3 hours, while keeping batch temperature below about 40° C. At about 20–25° C., ethyl acetate (5.8 L) was added to the slurry, followed by cooling to about –5° C. over about 1 hour. The slurry was aged at about –5° C. for about 1 hour and the solids isolated via filtration. The cake was washed with a chilled mixture of EtOAc/EtOH (9:1 v/v) (1×3.8 L), then the cake was washed with chilled EtOAc (2×3.8 L). The solids were dried in vacuo at about 25° C. to provide the above-titled compound.

$^1$H NMR (250 MHz, CDCl$_3$) δ 7.83–7.79 (d, 2H), 7.60–7.57 (d, 2H), 4.79 (s, 2H), 4.25 (s, 2H); $^{13}$C NMR (62.9 MHz, CDCl$_3$) 149.9, 139.8, 134.2, 131.2, 119.7, 113.4, 49.9, 49.5, 49.2, 48.8, 48.5, 48.2, 43.8.

EXAMPLE 3

Preparation of 1-(4-Cyanobenzyl)-2-Mercapto-5-Hydroxymethylimidazole

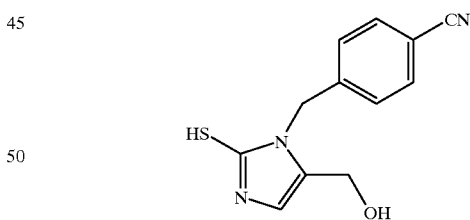

7% water in acetonitrile (50 mL) was added to a 250 mL roundbottom flask. Next, an amine phosphate salt (12.49 g), as described in Example 2, was added to the flask. Next potassium thiocyanate (6.04 g) and dihydroxyacetone (5.61 g) was added. Lastly, propionic acid (10.0 mL) was added. Acetonitrile/water 93:7 (25 mL) was used to rinse down the sides of the flask. This mixture was then heated to 60° C., aged for about 30 minutes and seeded with 1% thioimidazole. The mixture was then aged for about 1.5 to about 2 hours at 60° C. Next, the mixture was heated to 70° C., and aged for 2 hours. The temperature of the mixture was then cooled to room temperature and was aged overnight. The thioimidazole product was obtained by vacuum filtration.

The filter cake was washed four times acetonitrile (25 mL each time) until the filtrates became nearly colorless. Then the filter cake was washed three times with water (approximately 25-50 mL each time) and dried in vacuo to obtain the above-identified compound.

EXAMPLE 4

Preparation of 1-(4-Benzyl)-2-Mercapto-5-Hydroxymethylimidazole

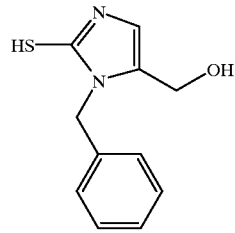

Following the procedure described for Example 3, but using a benzylamine salt, the title compound is obtained.

EXAMPLE 5

Preparation of 1-(4-Bromobenzyl) 2-Mercapto-5-Hydroxymethylimidazole

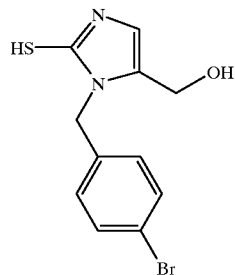

Following the procedure described for Example 3, but using bromobenzylamine salt, the title compound is obtained.

EXAMPLE 6

Preparation of 1-(4-Nitrobenzyl)-2-Mercapto-5-Hydroxymethylimidazole

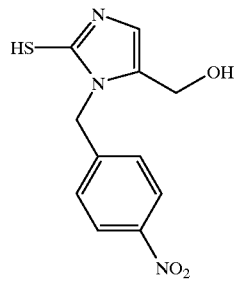

Following the procedure described for Example 3, but using nitrobenzylamine salt, the title compound is obtained.

EXAMPLE 7

Preparation of 1-(4-Cyanobenzyl)-5-Hydroxymethylimidazole

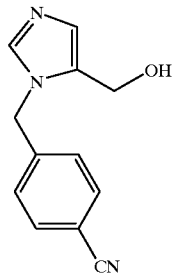

A 1L flask with cooling/heating jacket and glass stirrer (Lab-Max) was charged with water (200 mL) at 25° C. The thioimidazole (90.27 g), as described in Example 3, was added, followed by acetic acid (120 mL) and water (50 mL) to form a pale pink slurry. The reaction was warmed to 40° C. over 10 minutes. Hydrogen peroxide (90.0 g) was added slowly over 2 hours by automatic pump maintaining a temperature of 35–45° C. The temperature was lowered to 25° C. and the solution aged for 1 hour.

The solution was cooled to 20° C. and quenched by slowly adding 20% aqueous $Na_2SO_3$ (25 mL) maintaining the temperature at less than 25° C. The solution was filtered through a bed of DARCO G-60 (9.0 g) over a bed of SolkaFlok (1.9 g) in a sintered glass funnel. The bed was washed with 25 mL of 10% acetic acid in water.

The combined filtrates were cooled to 15° C. and a 25% aqueous ammonia was added over a 30 minute period, maintaining the temperature below 25° C., to a pH of 9.3. The yellowish slurry was aged overnight at 23° C. (room temperature). The solids were isolated via vacuum filtration. The cake (100 mL wet volume) was washed with 2×250 mL 5% ammonia (25%) in water, followed by 100 mL of ethyl acetate. The wet cake was dried with vacuum/$N_2$ flow and the above-titled compound was obtained.

$^1$H NMR (250 MHz, $CDCl_3$): δ 7.84–7.72 (d, 2H), 7.31–7.28 (d, 2H), 6.85 (s, 1H), 5.34 (s, 2H), 5.14–5.11 (t, 1H), 4.30–4.28 (d, 2H), 3.35 (s, 1H).

EXAMPLE 8

Preparation of 1-(4-Benzyl)-5-Hydroxymethylimidazole

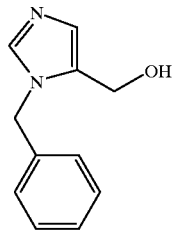

Following the procedure described for Example 7, but using a thioimidazole, as described in Example 4, the title compound is obtained.

EXAMPLE 9

Preparation of 1-(4-Bromobenzyl)-5-Hydroxymethylimidazole

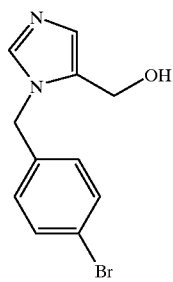

Following the procedure described for Example 7, but using a thioimidazole, as described in Example 5, the title compound is obtained.

EXAMPLE 10

Preparation of 1-(4-Nitrobenzyl)-5-Hydroxymethylimidazole

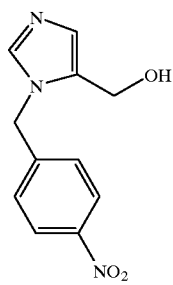

Following the procedure described for Example 7, but using a thioimidazole, as described in Example 6, the title compound is obtained.

EXAMPLE 11

Preparation of 1-(4-cyanobenzyl)-5-chloromethyl imidazole HCl salt

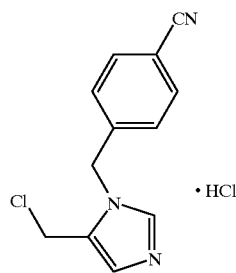

1-(4-Cyanobenzyl)-5-hydroxymethylimidazole (1.0 kg), as described in above in Example 7, was slurried with DMF (4.8 L) at 22° C. and then cooled to −5° C. Thionyl chloride (390 mL) was added dropwise over 60 min during which time the reaction temperature rose to a maximum of 9° C. The solution became nearly homogeneous before the product began to precipitate from solution. The slurry was warmed to 26° C. and aged for 1 h.

The slurry was then cooled to 5° C. and 2-propanol (120 mL) was added dropwise, followed by the addition of ethyl acetate (4.8 L). The slurry was aged at 5° C. for 1 h before the solids were isolated and washed with chilled ethyl acetate (3×1 L). The product was dried in vacuo at 40° C. overnight to provide the above-titled compound.

$^1$H NMR (250 MHz DMSO-$d_6$): δ 9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-$d_6$): $δ_c$ 139.7, 137.7, 132.7, 130.1, 128.8, 120.7, 118.4, 111.2, 48.9, 33.1.

EXAMPLE 12

Preparation of 1-(4-Cyanobenzyl)-5-Chloromethyl Imidazole HCl salt via addition of Hydroxymethylimidazole to Vilsmeier Reagent

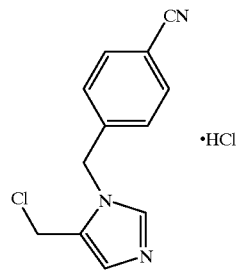

To an ice cold solution of dry acetonitrile (3.2 L, 15 L/Kg hydroxymethylimidazole) was added 99% oxalyl chloride (101 mL, 1.15 mol, 1.15 equiv.), followed by dry DMF (178 mL, 2.30 mol, 2.30 equiv.), at which time vigorous evolution of gas was observed. After stirring for about 5 to 10 min following the addition of DMF, solid hydroxymethylimidazole (213 g, 1.00 mol), as described above in Example 7, was added gradually. After the addition, the internal temperature was allowed to warm to a temperature of about 23° C. to about 25° C. and stirred for about 1 to 3 hours. The mixture was filtered, then washed with dry acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded approximately 93 to about 96% crystalline form of the chloromethylimidazole hydrochloride.

$^1$H NMR (250 MHz DMSO-$d_6$): δ 9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-$d_6$): $δ_c$ 139.7, 137.7, 132.7, 130.1, 128.8, 120.7, 118.4, 111.2, 48.9, 33.1.

EXAMPLE 13

Preparation of 1-(4-Cyanobenzyl)-5-Chloromethyl Imidazole HCl salt via addition of Vilsmeier Reagent to Hydroxymethylimidazole

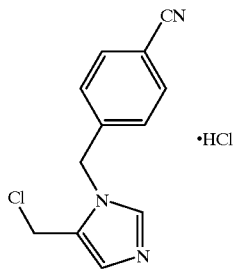

To an ice cold solution of dry DMF (178 mL, 2.30 mol, 2.30 equiv.) in dry acetonitrile (2.56 L, 12 L/Kg Hydroxymethylimidazole) was added oxalyl chloride (101 mL, 1.15 mol, 1.15 equiv). The heterogeneous mixture in the reagent vessel was then transferred to a mixture of hydroxymethylimidazole (213 g, 1.00 mol), as described above in Example 7, in dry acetonitrile (1.7 L, 8 L/Kg hydroxymethylimidazole). Additional dry acetonitrile (1.1–2.3 L, 5–11 L/Kg hydroxymethylimidazole) was added to the remaining solid Vilsmeier reagent in the reagent vessel. This, now nearly homogenous, solution was transferred to the reaction vessel at $T_i \leq +6°$ C. The reaction vessel temperature was warmed to a temperature of about 23° C. to about 25° C. and stirred for about 1 to 3 hours. The mixture was then cooled to 0° C. and aged 1 h. The solid was filtered and washed with dry, ice cold acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded approximately 92 to about 94% crystalline form of the chloromethylimidazole hydrochloride.

EXAMPLE 14

Preparation of 1-(4-Benzyl)-5-Chloromethyl Imidazole HCl salt

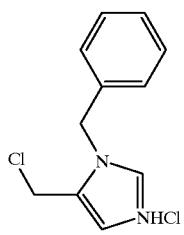

Following the procedure described for Example 12 or 13, but using 1-(4-benzyl)-5-hydroxymethylimidazole, the title compound is obtained.

EXAMPLE 15

Preparation of 1-(4-Bromobenzyl)-5-Chloromethyl Imidazole HCl salt

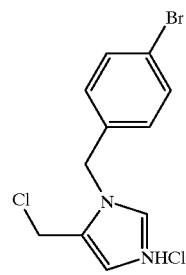

Following the procedure described for Example 12 or 13, but using 1-(4-bromobenzyl)-5-hydroxymethylimidazole, the title compound is obtained.

EXAMPLE 16

Preparation of 1-(4-Nitrobenzyl)-5-Chloromethyl Imidazole HCl salt

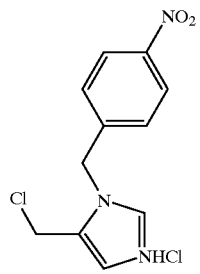

Following the procedure described for Example 12 or 13, but using 1-(4-nitrobenzyl)-5-hydroxymethylimidazole, the title compound is obtained.

What is claimed is:

1. A process for synthesizing a compound of formula I

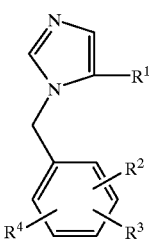

wherein $R^1$ is selected from H, unsubstituted or substituted $C_1$–$C_6$ alkyl, uns tbstituted or substituted aryl, unsubstituted or substituted heteroaryl, unsubstit ted or substituted aralkyl, or unsubstituted or substituted heteroaralkyl; and $R^2$, $R^3$ and $R^4$ are independently selected from H, halo, unsubstituted or substituted $C_1$–$C_6$ alkyl, unsubstituted or substituted $C_1$–$C_6$ alkoxy, OH, CN, $NO_2$, unsubstituted or s bstituted aryl, unsubstituted or substituted aryloxy, unsubstituted or substituted eteroaryl, trihalo- $C_1-C_6$ alkyl, trihalo-$C_1-C_6$ alkoxy, SO, $SO_2$, HC(O)($C_0-C_6$ alkyl)—, ($C_1-C_6$ alkyl)C(O)($C_0-C_6$ alkyl)—, —N($R^{10}$)$_2$, —NH$R^{10}$, —NHC(O)$R^{10}$, —N($R^{10}$)C(O)$R^{10}$, —NHSO$_2R^{10}$, and —N($R^{10}$)SO$_2R^{10}$;

$R^2$ and $R^3$ or $R^3$ and $R^4$, when located on adjacent carbon atoms, are unjoined or joined in a ring;

$R^{10}$ is independently selected from unsubstituted or substituted $C_1-C_6$ alkyl, unsubstituted or substituted aryl, and unsubstituted or substituted aralkyl;

or the pharmaceutically acceptable salts, thereof;

which comprises the steps of:
a) reacting a compound of formula A

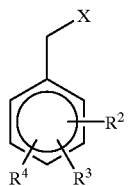

A (where X is a leaving group and $R^2$, $R^3$ and $R^4$ are as defined above) with hexamethylenetetramine in an alcohol to produce a hexamethyl netetramine salt of formula A1

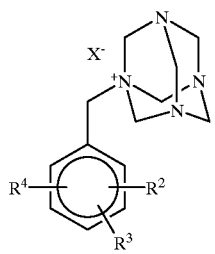

A1 where X, $R^2$, $R^3$ and $R^4$ are as defined above);

b) reacting one or more acids with a hexamethylenetetramine salt of formula A1 to produce an amine salt of formula B

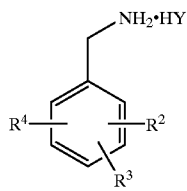

B (where Y is selected from a halide, a sulfonate, a phosphate or a sulfate and $R^2$, $R^3$ and $R^4$ are as defined above);

c) reacting the amine salt of formula B with a mixture of a reagent; which is selected from a hydroxyketone of formula C

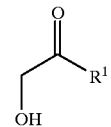

C or a hydroxyketone dimer of formula D

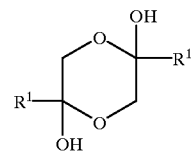

D (wherein $R^1$ is as defined above), and a thiocyanate, in an acidic solution to produce a mixture containing a mercapto-imidazole compound of formula E

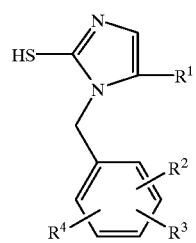

E (where $R^1$, $R^2$, $R^3$ and $R^4$ are as defined above); and
d) dethionating the mercapto-imidazole compound of formula E by reacting with an oxidizing agent in an acidic solution to produce the compound of formula I.

2. The process according to claim 1, wherein X of the compound of formula A is selected from a halide, a sulfonate, a phosphate or a sulfate.

3. The process according to claim 1, wherein the compound of formula A is an unsubstituted or substituted benzyl halide.

4. The process according to claim 1, wherein the alcohol is selected from from methanol, ethanol, n-propanol, i-propanol, butanol or an alkoxyethanol.

5. The process according to claim 1, wherein the acids are selected from anhydrous or aqueous phosphoric acid, HCl acid or propionic acid.

6. The process according to claim 1, wherein the reagent is selected from dihydroxyacetone, its dimeric equivalent or DHA, which repesents dihydroxyacetone in equilibrium with its dimeric equivalent.

7. The process according to claim 1, wherein the thiocyanate is selected from $C_1-C_6$ alkyl-SCN, aryl-SCN, heteroaryl-SCN, LiSCN, NaSCN, KSCN, CsSCN, MgSCN, CaSCN, HSCN, NH$_4$SCN or TMS-SCN.

8. The process according to claim 1, wherein the suitable acidic solution in step c) is a solution containing an acid and a solvent which is selected from acetonitrile, water, toluene or a mixture of these, with or without n-butanol.

9. The process according to claim 1, wherein the oxidizing agent is a peroxide which is selected from hydrogen peroxide, peracetic acid, MCPBA or t-BuOH.

10. The process according to claim 1, wherein the oxidizing agent is a nitrite which is selected from NaNO$_2$, KNO$_2$, or $C_1-C_6$ alkyl-NO$_2$.

11. The process according to claim 1, wherein the acidic solution in step d) is selected from aqueous methanesulfonic acid, acetic acid, propionic acid, trifluoroacetic acid or a mixture thereof.

12. A process for synthesizing a compound of formula I

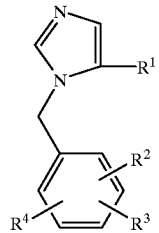

I wherein

R$^1$ is selected from H, unsubstituted or substituted C$_1$–C$_6$ alkyl, unsubstituted or substituted aryl, unsubstituted or substituted heteroaryl, unsubstituted or substituted aralkyl, or unsubstituted or substituted heteroaralkyl; and R$^2$, R$^3$ and R$^4$ are independently selected from H, halo, unsubstituted or substituted C$_1$–C$_6$ alkyl unsubstituted or substituted C$_1$–C$_6$ alkoxy, OH, CN, NO$_2$, unsubtituted or substituted aryl, unsubstituted or substituted aryloxy, unsubstituted or substituted heteroaryl, trihalo-C$_1$-c$_6$ alkyl, trihalo-C$_1$–C$_6$ aikoxy, SO, SO$_2$, HC(O)(C$_0$–C$_6$ akyl)—, (C$_1$–C$_6$ alkyl)C(O)(C$_0$–C$_6$ alkyl)—, —N(R$^{10}$)$_2$,—NHR$^{10}$,—NHC(O)R$^{10}$, —N(R$^{10}$)C(O)R$^{10}$,—NHSO$_2$R$^{10}$, and —N(R$^{10}$)SO$_2$R$^{10}$;

R$^2$ and R$^3$ or R$^3$ and R$^4$, when located on adjacent carbon atoms are unjoined or joined in a ring;

R$^{10}$ is independently selected from unsubstituted or substituted C$_1$–C$_6$ alkyl, unsubstituted or substituted aryl, and unsubstituted or substituted aralkyl;

or the pharmaceutically acceptable salts, thereof;

which comprises the steps of:
a) reacting a compound of formula A

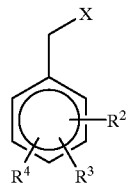

A (where X is a leaving group and R$^2$, R$^3$ and R$^4$ are as defined above) with hexamethylenetetramine in an alcohol to produce a hexamethylenetetramine salt of formula A1

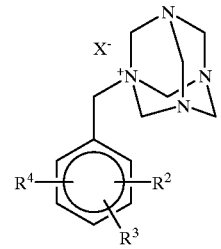

A1 where X, R$^2$, R$^3$ and R$^4$ are as defined above);

b) reacting the hexamethylenetetramine salt of formula A1 with phosphoric acid to produce a mixture containing an amine phosphate salt of formula B1

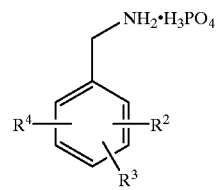

B1

(where R$^2$, R$^3$ and R$^4$ are as defined above);

c) reacting the mixture containing the amine phosphate salt of formula B1 with a mixture of a reagent, which is selected from a hydroxyketone of formula C

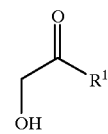

C or a hydroxyketone dimer of formula D

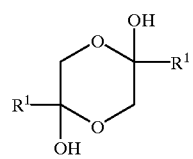

D (wherein R$^1$ is as defined above), and a thiocyanate, in an acidic solution to produce a mixture containing a mercaptoimidazole compound of formula E

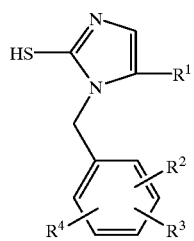

E (where R$^1$, R$^2$, R$^3$ and R$^4$ are as defined above);

d) dethionating the mercapto-imidazole compound of formula E by reacting with an oxidizing agent, selected from a peroxide or a nitrite, in an acidic solution;
e) adding a base compound; and
f) isolating the compound of formula I.

13. The process according to claim 12, wherein the base compound is selected from $NH_4OH$, $Na_2SO_3$, KOH, or NaOH.

14. The process according to claim 13, wherein the mixture containing the amine phosphate salt of formula Bi is heated to a temperature between about 65° C. to about 70° C. over about 15 to about 45 minutes and then cooled to a temperature of about 15° C. to about 35° C.

15. The process according to claim 14 wherein the mixture containing the mercapto-imidazole compound of formula E is heated to a temperature of about 45° C. to about 75° C. and thioimidazole seed is added.

16. A process for synthesizing A compound of formula I

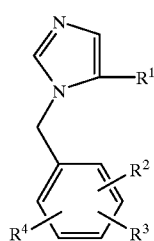

wherein
$R^1$ is selected from H, unsubstituted or substituted $C_1$–$C_6$ alkyl, uns bstituted or substituted aryl, unsubstituted or substitated heteroaryl, unsubstituted or substituted aralkyl, or unsubstituted or substituted heteroaralkyl; and
$R^2$, $R^3$ and $R^4$ are independently selected from H, halo, unsubstituted or substituted $C_1$–$C_6$ alky , unsubstituted or substituted $C_1$–$C_6$ alkoxy, OH, CN, $NO_2$, unsubstituted or substituted aryl, unsubstituted or substituted aryloxy, unsubstituted or substituted heteroaryl, trihalo-$C_1$–$C_6$ alkyl, trihalo-$C_1$–$C_6$ alkoxy, SO, $SO_2$, HC(O)($C_0$–$C_6$ alkyl)—, ($C_1$–$C_6$ alkyl)C(O)($C_0$–$C_6$ alkyl)—, —N($R^{10})_2$, —$NHR^{10}$, —NHC(O)$R^{10}$, —N($R^{10}$)C(O)$R^{10}$, —$NHSO_2R^{10}$, and —N($R^{10}$)$SO_2R^{10}$;
$R^2$ and $R^3$ or $R^3$ and $R^4$, when located on adjacent carbon atoms, are unjoined or joined in a ring;
$R^{10}$ is independently selected from unsubstituted or substituted $C_1$–$C_6$ alkyl, unsubstituted or substituted aryl, and unsubstituted or substituted aralkyl;
or the pharmaceutically acceptable salts, thereof;
which comprises the steps of:
a) reacting a compound of formula A

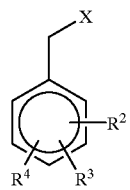

(where X is a leaving group and $R^2$, $R^3$ and $R^4$ are as defined above) with hexamethylenetetramine in an alcohol to produce a hexamethyl netetramine salt of formula A1

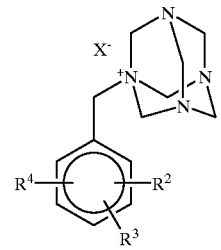

(where X, $R^2$, $R^3$ and $R^4$ are as defined above);

b) reacting the hexamethylenetetramine salt of formula A1 with HCl acid to produce a mixture containing an amine HCl salt;
c) reacting with an anti-solvent;
d) recovering a precipitated amine HCl salt and reacting with a base compound to produce a free base;
e) converting the free base to a salt by reacting with an acid, producing a mixture containing an amine salt of formula B2

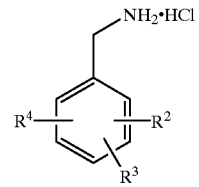

(where $R^2$, $R^3$ and $R^4$ are as defined above);

f) reacting the mi xture containing the amine salt of fonmula B2 with a mixture of a reagent, which is selected from a hydroxyketone of formula C

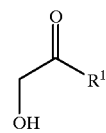

or a hydroxyketone dimer of formula D

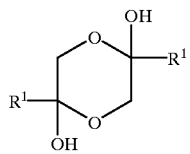

(wherein $R^1$ is as defined above), and a thiocyanate, in an acidic solution to produce a mixture containing a mercapto-imidazole compound of formula E

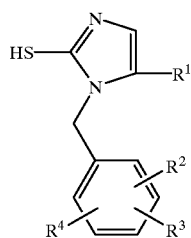

(where $R^1$, $R^2$, $R^3$ and $R^4$ are as defined above);
g) dethionating the mercapto-imidazole con pound of fonnula E by treating with an oxidizing agent, selected from peroxides and nitrites, in an acidic solution;
h) reacting with a base compound; and
i) isolating the compound of formula I.

17. The process according to claim 16, wherein the anti-solvent is selected from ethyl acetate, tetrahydrofuran, methyl-t-butyl-ether, toluene, acetonitrile, dimethyl formamide, alcohols, or carboxylic acids.

18. The process according to claim 17 wherein the base compound in step d) is selected from NaOH, KOH or $NH_4OH$.

19. The process according to claim 18, wherein the acid in step e) is aqueous HCl.

20. The process according to claim 19, wherein the suitable acidic solution in step f) is a solution containing an acid and a solvent which is selected from acetonitrile, water, toluene or a mixture of these, with or without n-butanol.

21. The process according to claim 20, wherein the acidic solution in step g) which is selected from aqueous methanesulfonic acid, acetic acid, propionic acid, trifluoroacetic acid or a mixture thereof.

22. The process according to claim 21, wherein the base compound in step h) is selected from $NH_4OH$, $Na_2SO_3$, KOH, or NaOH.

23. The process according to claim 16, wherein the mixture containing the mercapto-imidazole compound of formula E is heated to a temperature of about 45° C. to about 75° C. and thioimidazole seed is added.

24. The process according to claim 1, for synthesizing a compound of formula IA:

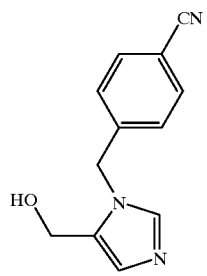

comprising the steps of:
a) reacting a cyanobenzyl bromide with hexamethylenetetramine in ethanol;
b) adding one or more acids to produce a cyanobenzylamine salt,
c) reacting the cyanobenzylamine salt with a mixture of dihydroxyacetone
and potassium thiocyanate, in acidic solution to produce a mixture containing 1-(4-Cyanobenzyl)-2-Mercapto-5-Hydroxymethylimidazole;

d) dethionating the 1-(4-Cyanobenzyl)-2-Mercapto-5-Hydroxymethylimidazole by reacting with hydrogen peroxide in an acidic solution;
e) adding ammonia;
f) isolating 1-(4-Cyanobenzyl)-5-Hydroxymethyl-imidazole of formula IA as a free base.

25. The process according to claim 24, wherein the acids in step b) are propionic acid and phosphoric acid.

26. A process for synthesizing a compound of formula IB

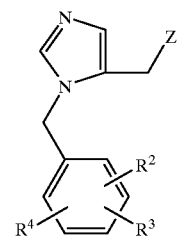

where $R^2$, $R^3$ and $R^4$ are independently selected from H, halo, unsubstituted or substituted $C_1$–$C_6$ alky , unsubstituted or substituted $C_1$–$C_6$ alkoxy, OH, CN, $NO_2$, unsubstituted or substituted aryl, unsubstituted or substituted aryloxy, unsubstituted or substituted eteroaryl, trihalo-$C_1$–$C_6$ alkyl, trihalo-$C_1$–$C_6$ alkoxy, SO, $SO_2$, HC(O)($C_0$–$C_6$ alkyl)—, ($C_1$–$C_6$ alkyl)C(O)($C_0$–$C_6$ alkyl)—, —N($R^{10}$)$_2$,—$NHR^{10}$, —NHC(O)$R^{10}$, —N($R^{10}$)C(O)$R^{10}$, —NHSO$_2$$R^{10}$, and —N($R^{10}$)SO$_2$$R^{10}$;

$R^2$ and $R^3$ or $R^3$ and $R^4$, when located on adjacent carbon aton S, are unjoined or joined in a ring;

$R^{10}$ is independently selected from unsubstituted or substituted $C_1$–$C_6$ alkyl, unsubstituted or substituted aryl, and unsubstituted or substituted aralkyl;

Z is selected from a halide, a sulfonate, a phosphate or a sulfate which comprises the step of:

reacting a 1-substituted benzyl-5-hydroxymethyl-imidazole compound of formula IC

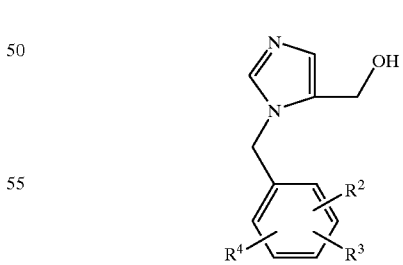

with an activating agent to produce a salt form of the compound of formula IB.

27. The process according to claim 26, wherein the activating agent is selected from a halogenating reagent, a sulfonating reagent, a sulfating reagent, a phosphonating reagent or a fluorinating reagent.

28. A process for synthesizing compound of formula ID

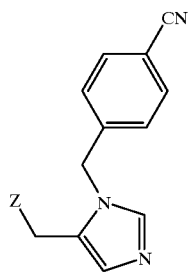
ID (where Z is a halide, a sulfate, a sulfonate or a phosphate)
comprising the step of:
reacting 1-(4-Cyanobenzyl)-5-Hydroxymethyl-imidazole of formula IA

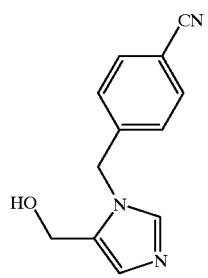
IA with an activating agent selected from a halogenating agent, a sulfating agent, a sulfonating agent, or a phosphonating agent to produce a compound of formula ID.

29. The process according to claim 28, wherein Z is a halide or a mesylate and the activating agent is a halogenating agent or a sulfonating agent.

30. A process for synthesizing compounds of formula IE

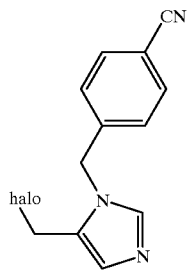
IE comprising the step of:

reacting 1-(4-Cyanobenzyl)-5-Hydroxymethyl-imidazole of formula IA

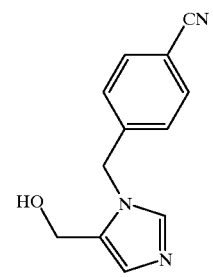
IA with a halogenating agent to produce a compound of formula IE.

31. The process according to claim 30, further comprises the step of:

reacting 1-(4-Cyanobenzyl)-5-Hydroxymethyl-imidazole of formula IA

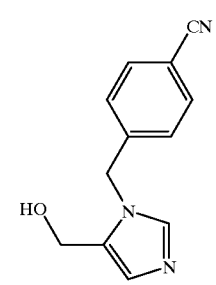
IA with Vilsmeier reagent to obtain 1-(4-Cyanobenzyl)-5-Chloromethyl-imidazole of formula IF:

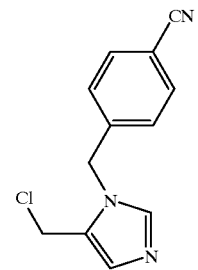
IF

* * * * *

UNITED STATES PATENT AND TRADEMARK OFFICE
CERTIFICATE OF CORRECTION

PATENT NO. : 6,140,508
DATED : October 31, 2000
INVENTOR(S) : David Askin, Jennifer A. Cowen, Peter E. Maligres, J. Christopher McWilliams, Margorie S. Waters It is certified that error appears in the above-identified patent and that said Letters Patent is hereby corrected as shown below:

Claim 1, column 34,
Line 59-60 should read as follows:
-- alkyl, unsubstituted or substituted aryl, unsubstituted or substituted heteroaryl, unsubstituted or substituted --.
Lines 66-67 should read as follows:
-- tuted or substituted aryl, unsubstituted or substituted aryloxy, unsubstituted or substituted heteroaryl, trihalo- --.
Column 35,
Line 2 should read as follows:
-- $(C_0\text{-}C_6\text{alkyl})$-, $(C_1\text{-}C_6\text{alkyl})C(O)(C_0\text{-}C_6\text{alkyl})$-, --.
Line 30 should read as follows:
-- duce a hexamethylenetetramine salt of formula A1 --.

Claim 12, column 37,
Line 31 should read as follows:
-- unsubstituted or substituted $C_1\text{-}C_6$alkyl, unsubstituted --.
Line 35 should read as follows:
-- $C_1\text{-}C_6$ alkyl, trihalo-$C_1\text{-}C_6$ alkoxy, SO, $SO_2$, HC(O) --.

Claim 14, column 39,
Line 11 should read as follows:
-- mixture containing the amine phosphate salt of formula B1 --.

Claim 16, column 39,
Line 19 should read as follows:
-- 16. A process for synthesizing a compound of formula I --.
Lines 34-36 should read as follows:
-- alkyl, unsubstituted or substituted aryl, unsubstituted or substituted heteroaryl, unsubstituted or substituted aralkyl, or unsubstituted or substituted heteroaralkyl; --.
Column 40,
Line 1 should read as follows:
-- duce a hexamethylenetetramine salt of formula A1 --.
Lines 41-42 should read as follows:
-- f) reacting the mixture containing the amine salt of formula B2 with a mixture of a reagent, which is --.

UNITED STATES PATENT AND TRADEMARK OFFICE
CERTIFICATE OF CORRECTION

PATENT NO. : 6,140,508
DATED : October 31, 2000
INVENTOR(S) : David Askin, Jennifer A. Cowen, Peter E. Maligres, J. Christopher McWilliams, Margorie S. Waters It is certified that error appears in the above-identified patent and that said Letters Patent is hereby corrected as shown below:

Claim 16, column 41,
Line 14-15 should read as follows:
-- g) dethionating the mercapto-imidazole compound of formula E by treating with an oxidizing agent, --.

Claim 26, column 42,
Line 29 should read as follows:
-- stituted or substituted heteroaryl, trihalo-$C_1$-$C_6$ alkyl, trihalo- --.
Line 36 should read as follows:
-- atoms, are unjoined or joined in a ring; --.
Line 42 should read as follows:
-- sulfate; --.

Signed and Sealed this

Eleventh Day of September, 2001

*Attest:*

NICHOLAS P. GODICI
*Attesting Officer*   *Acting Director of the United States Patent and Trademark Office*